United States Patent
Vogt

Patent Number: 5,414,943
Date of Patent: May 16, 1995

[54] ANATOMICAL MEASURING TAPE WITH INDICATOR

[76] Inventor: Katie Vogt, 275 Engle St., Apt. B2, Englewood, N.J. 07631

[21] Appl. No.: 150,812

[22] Filed: Nov. 12, 1993

[51] Int. Cl.$^6$ .................................................. G01B 3/10
[52] U.S. Cl. .................................... 33/764; 33/765; 33/759; 33/512
[58] Field of Search ............... 33/764, 765, 758, 759, 33/767, 511, 512, 514.2, 555.4

[56] References Cited

U.S. PATENT DOCUMENTS

| | | | |
|---|---|---|---|
| 208,346 | 9/1878 | Taylor | 33/764 |
| 870,884 | 11/1907 | Holinger | 33/764 |
| 940,256 | 11/1909 | Kennedy et al. | 33/514.2 |
| 1,216,418 | 2/1917 | Crolan | 33/765 |
| 2,205,626 | 6/1940 | Mason | 33/514.2 |
| 2,230,668 | 2/1941 | Ohrtmann | 33/764 |
| 2,240,753 | 5/1941 | Bouchard et al. | 33/764 |
| 2,271,725 | 2/1942 | Tunnicliff | 33/514.2 |
| 3,426,435 | 2/1969 | Ballard et al. | 33/767 |
| 3,885,314 | 5/1975 | Banas, Sr. | 33/764 |
| 4,506,446 | 3/1985 | Mirhell | 33/764 |

FOREIGN PATENT DOCUMENTS

| | | | |
|---|---|---|---|
| 619269 | 9/1935 | Germany | 33/2 R |
| 361776 | 6/1962 | Switzerland | 33/2 R |

Primary Examiner—Thomas B. Will
Attorney, Agent, or Firm—Terrance L. Siemens

[57] ABSTRACT

A measuring device having two measuring tapes held on separate reels in a housing. The housing has two windows for displaying measurement indicia appearing on each tape. The tapes are spring biased toward the fully wound condition. Each tape has a button controlled clutch locking each respective tape in an extended condition. In a preferred application, a user draws a first tape around her torso just below the breasts, connects the tape to the end of the second tape at the housing, and locks this tape when taut. The device is moved upwardly, now encircling the breasts also, and the second tape is extended to accommodate the additional girth. The second clutch locks the second tape in position. The device is removed from the user's body, and sizes displayed in the windows are read. The first tape measures and indicates rib cage girth, and the second tape converts the additional measurement to cup sizes. The windows expose only the relevant data from each respective tape, maintaining the data visible while the tapes are locked in the extended condition. When the clutches are released, both reels rewind.

5 Claims, 3 Drawing Sheets

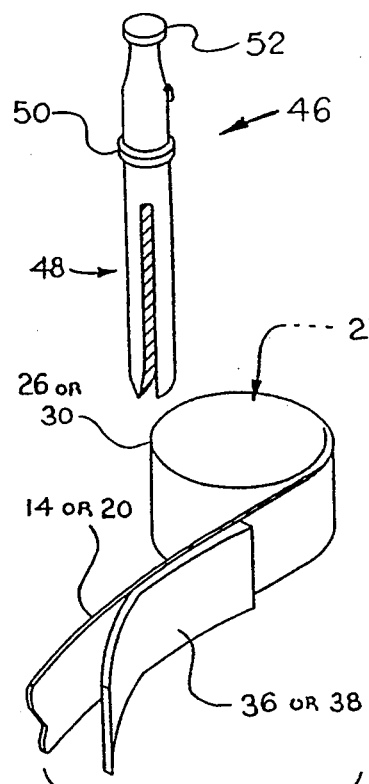
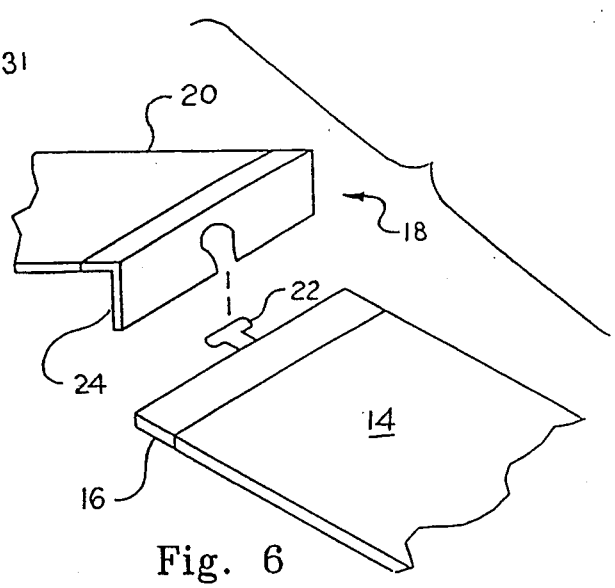
Fig. 5        Fig. 6
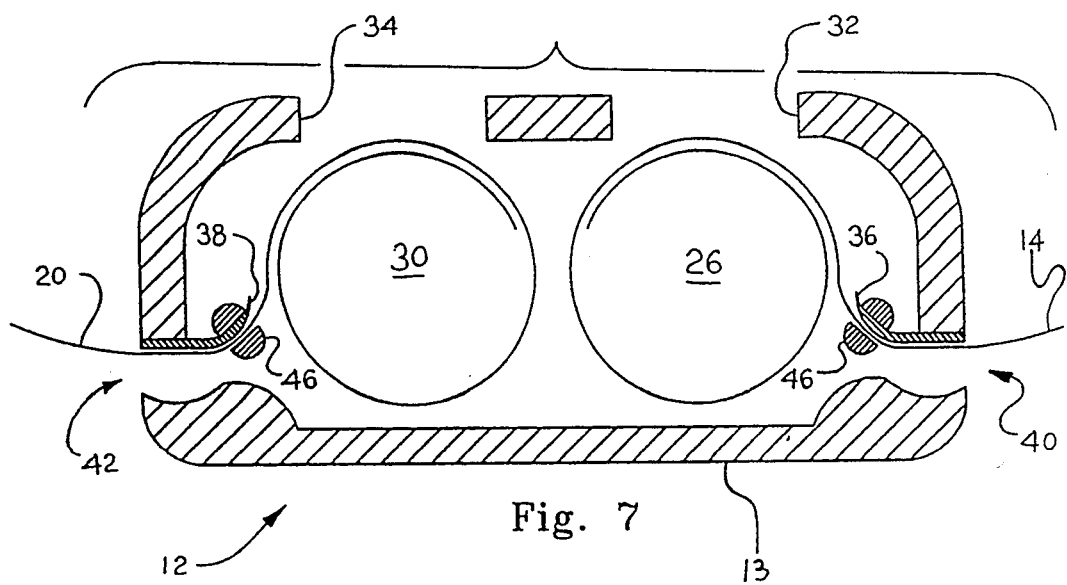
Fig. 7

ANATOMICAL MEASURING TAPE WITH INDICATOR

BACKGROUND OF THE INVENTION

1. Field of the Invention

The present invention relates to a device for making plural anatomical measurements, and displaying the results. The purpose of the device is to identify an appropriate apparel size for a user. More particularly, the specific embodiment chosen as an exposition of the details of the invention is a double tape type device which provides a direct readout of the two measurements determining the size of a woman's brassiere. The routinist could easily determine how the principles of this invention could be extended to provide the two appropriate measurements for any article of clothing requiring two measurements. Many such items of clothing exist. For example, mens' pants sizes consist of the two measurements that represent the waist and the inseam. In the most general sense, the invention need not be confined to measuring garment sizes at all. Any measurement that needs a clear and unambiguous double readout could be made with this invention. For example, the length and girth of a fish could be easily and rapidly recorded.

Thus it can be seen that the potential fields of use for this invention are myriad, and the particular preferred embodiment described herein is in no way meant to be limiting the particular field chosen for exposition of the details of the invention.

2. Description of the Prior Art

Adaptation of a measuring tape, or the like, to determine appropriate apparel sizes has long been attempted, as will be seen from the prior art. The reader will note that most, if not all, apparel tapes require a second person to measure the first.

U.S. Pat. No. 2,559,501, issued to Fred V. Graf on Jul. 3, 1951, discloses a device which is essentially donned in the manner of a brassiere, there being graduated indicia provided on transparent cups for measuring breast size, in addition to indicia provided on the strap encircling the torso for determining bust girth. There is a buckle provided between cups to establish a satisfactory separation of the breasts. This device must be manipulated in at least six operational steps in order to yield results. The inventor teaches assistance by another person in employing the device. Contrast this with the instant invention wherein a self-operated device is provided which can be easily manipulated and which provides a direct readout of the final clothing size for which the tape has been designed.

U.S. Pat. No. 2,946,125, issued to Bernard Gittelson on Jul. 26, 1960, discloses a harness comprising five graduated straps. Gittelson produces indirect measurements, i.e., requiring calculation of measured data, as opposed to displaying a final, usable value or standard size.

A measuring tape having measurements on opposing sides is seen in U.S. Pat. No. 3,292,261, issued to Madeline L. Hayes on Dec. 20, 1966. The tape is held encircling the torso, and a benchmark indicates an appropriate size. A separate tape member is then attached, so that markings indicative of cup size become visible. The tape is then again placed around the torso, this time encircling the breasts, and one marking indicative of cup size is brought into registry with the previously determined torso girth.

U.S. Pat. No. 3,849,886, issued to Nola D. Weyrick et al. on Nov. 26, 1974, discloses a tape measure adapted to include removable markers for recording measurements. When the tape encircles the body, one end meeting the tape at an intermediate point, a marker is adhered at that point. The marker includes indicia identifying which measurement resulted in the indicated value.

U.S. Pat. No. 4,211,011, issued to Ilamae W. Jacobson on Jul. 8, 1980, discloses a body garment incorporating a plurality of body encircling measurement tapes. Each tape is adhered in its snug position, and indicates a measured circumference. After all tapes are adhered, they remain in place as a part of the garment to be worn.

U.S. Pat. No. 4,875,296, issued to John P. Holzmeister et al. on Oct. 24, 1989, discloses a device comprising a tape measure and a frictional retaining member. The tape is passed around the body of a user, and is passed through the retaining member. The device can be held in this position by pulling with one hand, the other hand remaining free to record the measurement. The measurement is determined in similar fashion to that employed in reading a standard tape measure; that is, aligning the zero dimension end with a measured value. The Holzmeister et al. invention enables holding the tape measure in its deployed position with but a single hand.

None of the above inventions and patents, taken either singly or in combination, is seen to describe the instant invention as claimed.

SUMMARY OF THE INVENTION

The present invention provides a tape measure which can be successfully used by one person to measure one's own body. It can therefore be used by women who wish to determine apparel size, by themselves, and not be reliant upon an assistant.

A housing encloses two reels, each paying out a measuring tape. A first tape is extended around the body, and locked in the extended condition, once its free end has encircled the torso and met the housing. The reels are spring biased to rewind, so that the device is retained in its position encircling the body by resilient grip. This frees the user's hands to manipulate the device, repositioning the same about the bust.

Since the first tape is locked to extend from the housing the distance equivalent to the girth, the second tape is now payed out to accommodate the additional girth. The second tape can also be locked. Each tape displays the paid out dimension through windows formed in the housing, and these values are maintained if the tapes are locked in position. The device can be removed from the body, and the values displayed can be clearly read.

The novel measuring device is readily operated by one person, and the values obtained thereby are easily read once the device is removed from the body. The tapes are quickly rewound by releasing the two locks.

The device is self-supporting in place on the body, in both positions, so that the user can remove her hands therefrom, and reposition the hands for subsequent handling thereof.

The instant invention avoids certain situations encountered in the prior art, such as requiring further calculations or conversions to arrive at final, usable values, preferably in the form of recognized standard sizes. Instead, the device reads out final apparel sizes.

This is accomplished by incorporating a well known formula in the intimate apparel industry as will be hereinafter described. The first tape measures the rib cage ($R_1$) under the bust and is calibrated such that the readout is the actual measurement plus 5 ($R_1+5$), to correspond to the band size on a brassiere. The second tape is calibrated to incorporate the formula wherein the cup size corresponds to the bust size measurement ($R_2$) minus the rib cage measurement plus five ($R_2-(R_1+5)$).

Accordingly, it is a principal object of the invention to provide an anatomical measuring device which is readily operable by one person in full and complete privacy.

It is another object of the invention to provide an anatomical measuring device which makes all calculations, and displays final, usable values.

It is another object of the invention to provide an anatomical measuring device in which the displayed final useable values are permanently and fixedly displayed until deliberately removed in preparation for another measurement.

It is a further object of the invention to provide an anatomical measuring device which is self-supporting on the body of the user.

It is an additional object of the invention to provide an anatomical measuring device which is uncomplicated, and which employs well known apparatus, such as tape measures, whereby it is quickly mastered by a user.

Another object of the invention is to provide an anatomical measuring device which maintains the displayed values until released by the user.

It is a final object of the invention to provide an anatomical measuring device which stores its measuring tapes within a compact housing, and biases the tapes into the stored condition.

It is a general goal of the invention to provide improved elements and arrangements thereof in an apparatus for the purposes described which is inexpensive, dependable and fully effective in accomplishing its intended purposes.

It is submitted that the present invention meets or exceeds all the above objects and goals. Upon further study of the specification and appended claims, further objects and advantages of this invention will become apparent to those skilled in the art.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 5 is a perspective detail view of a locking mechanism, a partial measuring tape, and a guide member, shown isolated from the rest of the invention, and drawn to enlarged scale.

FIG. 6 is a perspective detail view of connection members for attaching the ends of the tapes together, drawn to enlarged scale.

FIG. 7 is a diagrammatic, cross sectional, top plan view of the housing and its principal components, drawn to enlarged scale.

DETAILED DESCRIPTION OF A PREFERRED EMBODIMENT

Figure 1:
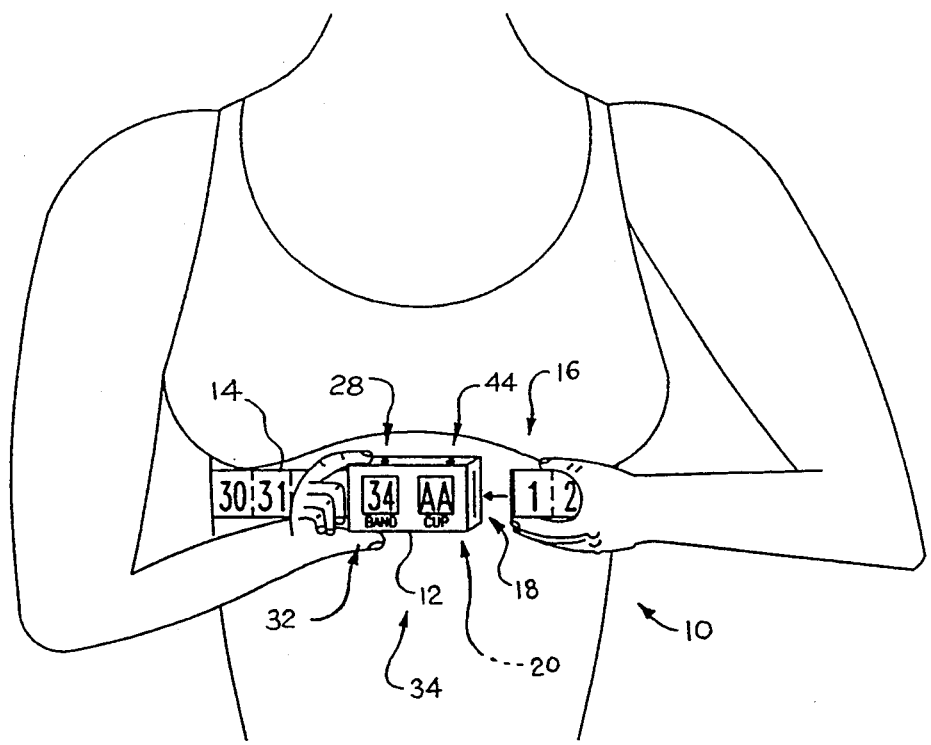
FIG. 1 is an environmental, front elevational view of the invention, showing a first measurement step.
Figure 4:
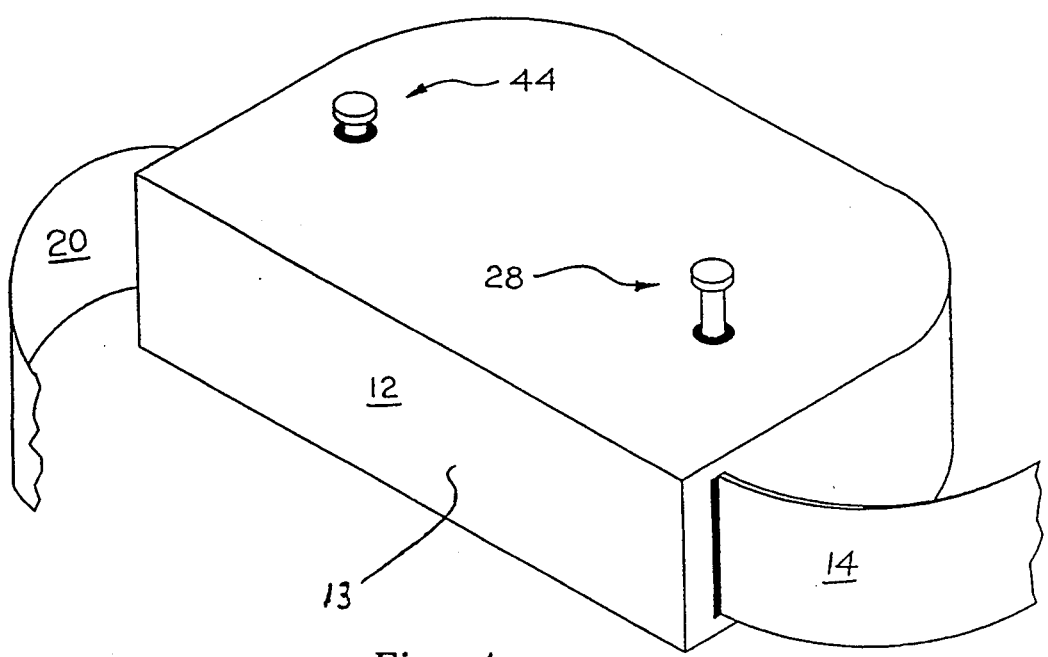

Turning now to FIG. 1 of the drawings, the anatomical measuring device 10 is shown placed about the torso of a user so as to take the first of two measurements. A housing 12 containing two measuring tapes is held in one hand at any convenient point below the breasts, and a first measuring tape 14 is grasped in the other hand and paid out. Free end 16 is held in the second hand, passed around the back, and is returned to housing 12. Free end 16 can be latched to free end 18 of second measuring tape 20 by interengaging members 22, 24 (see FIG. 6) disposed at respective free ends 16, 18. At this point, device 10 is self-supporting, resiliently clinging to the torso under tension imposed by its respective reel 26 (see FIG. 7), which has a spring 27 (see FIG. 5) biasing reel 26 to rewind. As the device 10 is held under this tension, a flat wall 13 (best shown in FIG. 4) of the housing 12 is held substantially in full contact with the user's body, to guarantee the accuracy of the measurements obtained by the device 10.

Figure 2:
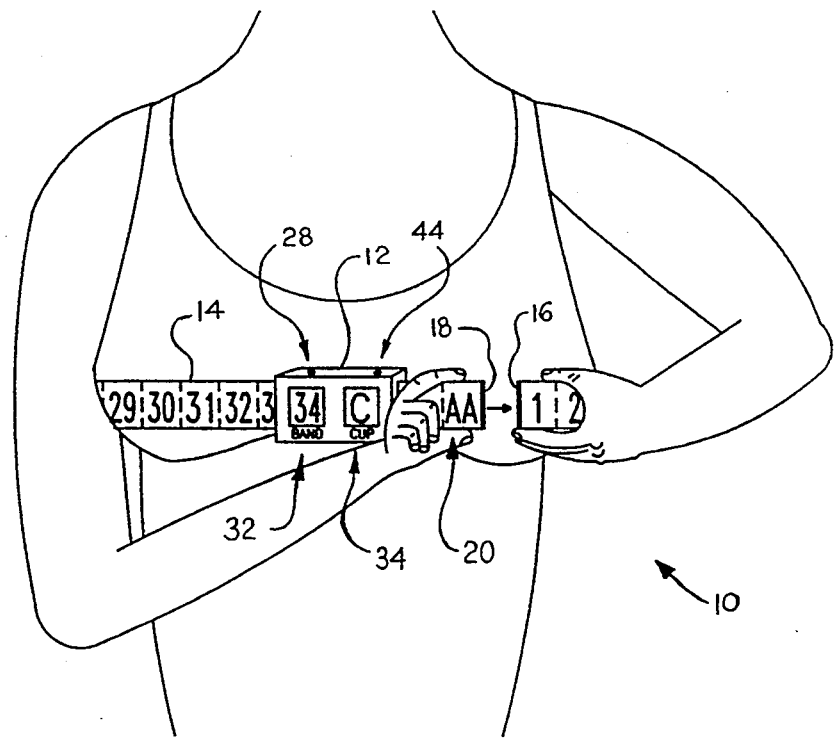
FIG. 2 is an environmental, front elevational view of the invention, showing a second measurement step.

A first locking mechanism 28, which will be explained hereinafter, immobilizes first measuring tape 14. Free ends 16, 18 are unlatched, and device 10 is repositioned over the bust, as shown in FIG. 2. Second measuring tape 20 wound on reel 30 is paid out until its respective free end 18 meets free end 16 of first measuring tape 14. Reel 30 includes a second spring 31 also biasing its respective reel 30 to rewind.

Indicia are placed on first and second measuring tapes 14, 20, arranged to allow for the width of housing 12, and located so as to be visible in windows 32, 34 formed in housing 12. First measuring tape 14 bears indicia corresponding to inch, or metric values, if desired, increments within a generally accepted range encompassing those chest sizes recognized by the apparel industry. Second measuring tape 20 bears indicia in the form of letters, arranged to correspond to brassiere cup sizes recognized by the apparel industry. Low or small values appear on free ends 16 and 18, so that the maximum measured value is framed in window 32 or 34 when a respective measuring tape 14 or 20 is extended.

Reels 26 and 30 are disposed adjacent one another, and hence the wound portions of measuring tapes 14 and 20 are adjacent. An alphanumeric value is thus collectively displayed in windows 32 and 34 when the second measurement is taken. This value can be remembered or recorded, and no further calculation or conversion is required.

With reference to FIG. 7, housing 12 is seen to enclose reels 26 and 30. A portion of each measuring tape 14 or 20 passes beside a thin metal guide 36 or 38, and passes through a slot 40 or 42 to the exterior of housing 12.

Locking mechanisms 28, 44 will now be explained, both being substantially identical, but mirror image to one another. A bore (not shown) formed in housing 12 accepts a generally cylindrical locking member 46, better seen in FIG. 5, having a clevis 48 which straddles both measuring tape 14 or 20 and respective guide 36 or 38. When pushed downwardly, locking member 46 resiliently pinches measuring tape 14 or 20 to guide 36 or 38, thus immobilizing measuring tape 14 or 20. When locking member 46 is pulled upwardly, grip on measuring tape 14 or 20 is relaxed, and respective reel 26 or 30 rewinds measuring tape 14 or 20 if not restrained by being held by hand.

A shoulder 50 formed in locking member 46 abuts a corresponding shoulder (not shown) in housing 12, thereby limiting vertical travel, and preventing removal of locking member 46 from housing 12.

Figure 3:
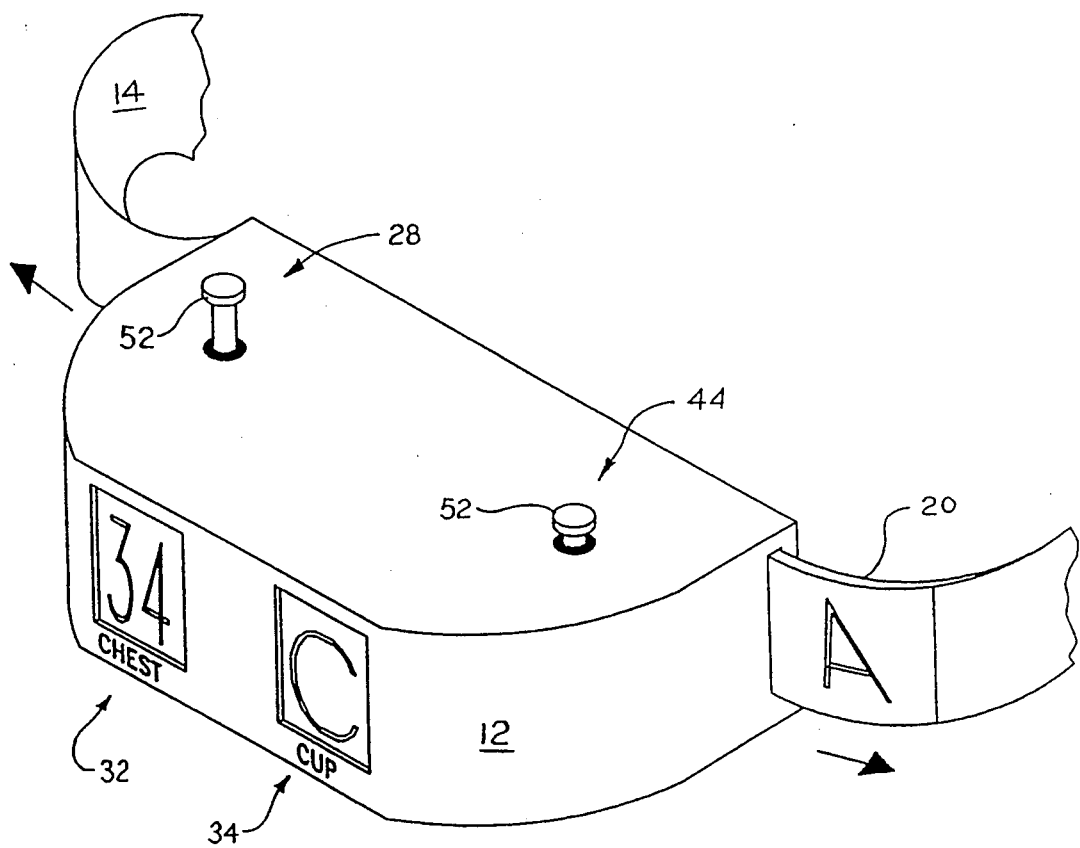
FIGS. 3 and 4 are, respectively, front and rear perspective views of the housing of the invention, with measuring tapes broken away, and drawn to enlarged scale.

As seen in FIG. 3, there are two locking mechanisms 28,44. One locking mechanism 44 is shown pushed down in the locked position at the right of this view, and the other locking mechanism 28 is shown pulled up, in the released position. Each locking mechanism 28 or 44 has a head 52 enabling grasping by a user, so that it may be readily pulled into the released position.

Thus it will be seen that an uncomplicated yet effective measuring device is disclosed which is easily grasped and operated, which displays measurement values in final format, and is readily operated by a person taking her own measurements.

It is to be understood that the present invention is not limited to the embodiment described above, but encompasses any and all embodiments within the scope of the following claims.

I claim:

1. An anatomical measuring device for measuring brassiere sizes comprising:

a housing, said housing having a flat wall configured such that is held in contact with an anatomical surface to be measured;

a first measuring tape with numeric indicia thereon, and having a first reel, said first measuring tape being unwindable from said first reel to an extended position;

a second measuring tape with alphabetic indicia thereon, and having a second reel, said second measuring tape being unwindable from said second reel to an extended position, said first and second measuring tapes and said first and second reels being disposed within said housing;

means defining a first and second windows in said housing, said first and second windows disposed such that the numeric and alphabetic indicia appearing on said first and second measuring tape, respectively, are visible through said first and second windows, respectively;

first locking means for independently fixing said first measuring tape in an extended position; whereby when said wall of said housing is held against a first anatomical surface to be measured at a rib cage level of a user, said first measuring tape is extended and locked in position, and a first numeric reading, corresponding to a band size of the brassiere to be worn by the user, can be taken through said first window, and when said wall of said housing is held against a second anatomical surface to be measured at a bust line level of the user, said second measuring tape is extended to meet said first measuring tape, and an alphabetic reading, corresponding to the difference between said first numeric reading and a bust line circumference of the user to denote a cup size of the brassiere to be worn by the user, can be taken through said second window.

2. The anatomical measuring device according to claim 1, wherein said first and second reels further include spring biasing means, said biasing means urging said first and second reels to rewind.

3. The anatomical measuring device according to claim 1, wherein said first locking means is manually adjustable between a locked and an unlocked position.

4. The anatomical measuring device according to claim 1, further including a second locking means for fixing said second measuring tape in an extended position.

5. The anatomical measuring device according to claim 1, wherein each of said first and second measuring tapes have a respective free end, said free ends including means for mutual interengagement.

* * * * *